United States Patent
Mo

(10) Patent No.: US 6,631,297 B1
(45) Date of Patent: Oct. 7, 2003

(54) ELECTRICAL CLINICAL APPARATUS AND ELECTRICAL STIMULATION METHOD USING VARIANT ASSIGNMENT METHOD

(76) Inventor: Seung-Kee Mo, #602, Blueheights, 379-3 Yangjae-dong, Seocho-ku, Seoul, 137-130 (KR)

( * ) Notice: Subject to any disclaimer, the term of this patent is extended or adjusted under 35 U.S.C. 154(b) by 307 days.

(21) Appl. No.: 09/693,758

(22) Filed: Oct. 20, 2000

(30) Foreign Application Priority Data

May 18, 2000 (KR) .................................... 2000-26694

(51) Int. Cl.[7] .................................................. A61N 1/18
(52) U.S. Cl. .......................... 607/62; 607/46; 607/63; 607/72; 128/733; 600/546
(58) Field of Search ............................ 607/46, 48–49, 607/60, 62–63, 59, 70, 72, 74, 67, 116, 129, 138, 148, 152; 128/733, 905; 600/546, 591, 29

(56) References Cited

U.S. PATENT DOCUMENTS

| | | | | |
|---|---|---|---|---|
| 4,881,526 A | * | 11/1989 | Johnson et al. ............ 128/24.5 |
| 5,549,656 A | * | 8/1996 | Reiss ......................... 607/148 |
| 6,076,011 A | * | 6/2000 | Hoover ....................... 600/546 |
| 6,289,245 B1 | * | 9/2001 | Mo et al. ..................... 607/41 |

* cited by examiner

Primary Examiner—Teresa Walberg
Assistant Examiner—Shawntina Fuqua
(74) Attorney, Agent, or Firm—Sheridan Ross PC

(57) ABSTRACT

An electrical stimulation method and an electrical clinical apparatus using a variant assignment method applied in treatment of dysfunction such as urinary incontinence is disclosed. The electrical clinical apparatus includes: a central control device for forming a plurality of protocols by converting frequencies of the electrical signals to be applied to a body part, and for generating a plurality of variants by assembling the protocols, and for respectively selecting protocols or variants to be assigned to each channel of the electrode out of the protocols and variants; a memory device for storing the protocols or variants produced by the central control device, or for re-inputting the stored protocols or variants back to the central control device according to a predetermined program; and an output device for outputting the selected protocol or variant to each channel of the electrode.

16 Claims, 6 Drawing Sheets

ELECTRICAL CLINICAL APPARATUS AND ELECTRICAL STIMULATION METHOD USING VARIANT ASSIGNMENT METHOD

FIELD OF THE INVENTION

The present invention relates to an electrical stimulation method and an electrical clinical apparatus including electrode for detecting electromyogram (EMG) signals from or for applying electrical stimulation signals to a body part; and, more particularly, an electrical stimulation method and an electrical clinical apparatus using variant assignment method applied in treatment of dysfunction such as urinary incontinence.

DESCRIPTION OF THE PRIOR ARTS

An electrical clinical apparatus has been used in treatment of such dysfunction as urinary incontinence, constipation and fecal incontinence, pain relief, rehabilitation, and frigidity associated with reinnervation of damaged nerve such as pelvic floor muscle. Most electrical clinical apparatus use electromyogram (EMG) signals or current pulses as intensity of EMG is proportional to contractile force of vaginal (anal) muscle while current pulse is effective in nerve reinnervation.

Although the frequency of EMG signals mostly lies in between approx. 20 and 800 Hz emitting higher frequency components than other bio signals, a conventional mechanism of energy transmission method contrarily uses only a few frequencies (12.5 Hz and/or 50 Hz) without using most of the wide range of frequency bandwidth.

FIGS. 1, 2A and 2B illustrate a conventional electrical clinical apparatus. FIG. 1 illustrates frequency movements in an electrical stimulation method using a conventional frequency fixed assignment method, and FIGS. 2A and 2B illustrate electrodes functioning with fixed frequency according to the electrical stimulation method. A pair of metal rings wound around an electrode is called a channel which is an essential requirement of an electrode structure for conducting electric current.

As seen in above figures, in order to apply stimulation with a specific fixed frequency (F1 or F2) repeatedly, a conventional electrical clinical apparatus fixed to a specific frequency such as 12.5 Hz or 50 Hz on a specific channel 210 or 220 of an electrode 200 included therein. Here, the variation factor of the electrode is a regulation of electric current (voltage) based on the ratio between stimulating duration and resting duration.

However, the conventional apparatus had a problem of discomfort the patient had to suffer from when the specific frequency does not fit a patient's body. Besides, even though an electrical stimulation frequency fits a patient's body, continuous stimulation onto a certain region with the same fixed frequency involves the problem of discomfort (usually one session of electrical stimulation takes 15~30 minutes) Electro-physiologically cell of the skin so easily adapt to the frequency that in the treatment thereafter the sense from electrical stimulation become dull, and thus causing discomfort to the patients. Such a problem may directly lead to discontinued exercise or discourage patient's endeavor on their treatment.

Therefore, the conventional electrical clinical apparatus had therapeutic value only in case of a patient who fits to such a frequency. It is because the patient's condition vary in terms of age, sex, race, physical constitution and so on. In short, the uniform treatment of various types of patients with only a specific fixed frequency is unreasonable in itself. The electrical stimulation has a therapeutic value of 90% or more when the stimulation fits a patient while it did not show any effects when it did not fit a patient, accordingly, it is true that medical circles regarded electrical stimulation as a kind of inconsistent therapy.

In addition, above-mentioned discomfort or inconsistent therapeutic value was pointed out as the mere side effects of the electrical stimulation in a medical publication titled "Clinical postreproductive gynecology" by Samir N. Hajj and Wendy J. Evans (Appleton & Lange, Inc., pages 308, line 25).

In addition to the problems, the conventional electrical clinical apparatus displays in a uniform pattern the target waveforms, being presented to patients, as an assessing tool of one's own EMG signals, and thus the patients exercising to the display gets to feel tedious, which often makes patient unable to continue pelvic muscle exercise or EMG biofeedback exercise for a sufficient time.

In order to improve above-mentioned problems, the present applicant applied for: the Korean patent application No.98-5998 filed on Feb. 25, 1998, entitled "Urinary Incontinence Therapeutic Apparatus using EMG Envelope Signal"; the Korean patent application No.98-29206 filed on Jul. 21, 1998, entitled "Electrical Apparatus for Medical Treatment using EMG Envelope Signal", claiming domestic priority based on the Korean patent application file No.98-5998; The Korean patent application No.99-4237 filed on Feb. 8, 1999, entitled "Electrical Clinical Apparatus including Protective Circuit."

SUMMARY OF THE INVENTION

An object of the present invention is to provide an electrical clinical apparatus and electrical stimulation method for enabling consistent treatment without discomfort as well as for solving problems caused by use of only a few fixed frequencies.

In accordance with an aspect of the present invention, there is provided an electrical clinical apparatus including an electrode, which is in contact with a body part or is inserted into a body cavity, for detecting EMG signals thereof or for applying electrical stimulation signals thereto, the electrical clinical apparatus comprising: a central control device for forming a plurality of protocols by converting frequencies of the electrical signals to be applied to a body part, and for generating a plurality of variants by assembling the protocols, and for respectively selecting protocols or variants to be assigned to each channel of said electrode out of the protocols and variants; a memory device for storing the protocols or variants produced by said central control device, or for re-inputting the stored protocols or variants back to said central control device according to a predetermined program; and an output device for outputting the selected protocol or variant to each channel of said electrode, wherein said electrode assigned with the protocols or variants of choice includes a single- or multi-channel in the same or opposite direction of current and wherein the selected protocols or variants are characterized by the same or opposite electric characteristics each other.

In accordance with an embodiment of the present invention, there is provided an electrical clinical apparatus including an electrode, which is in contact with a body part or is inserted into a body cavity, for detecting EMG signals thereof or for applying electrical stimulation signals thereto, the electrical clinical apparatus comprising: a central control device for assigning each channel of said electrode with the protocols or the variants which are inputted through a communication equipment connected externally into said electrical clinical apparatus, wherein the protocols are formed by a conversion of electric signals to be delivered to a said body part in terms of pulse width, duty ratio, intensity/voltage of supplied electric current, burst duration, and inter-burst interval as well as frequencies and the variants are formed by assembling the protocols; and an output device for outputting the assigned protocols or variants by said central control device into each channel of said electrode, wherein said electrode assigned with the protocols or variants includes a single- or multi-channel with the same or opposite direction of electric currents on each channel and wherein the assigned protocols or variants have the same or opposite electrical characteristics each other.

In accordance with another aspect of the present invention, there is provided an electrical stimulation method through an electrical clinical apparatus including an electrode and a central control device for controlling said electrode, wherein said electrode is in contact with a body part or is inserted into a body cavity for stimulating thereto by applying electrical signals, the electrical stimulation method comprising the steps of: a) creating a protocol library and storing the protocol library in said central control device or a memory of the electrical clinical apparatus, wherein the protocol library includes protocols formed by a frequency conversion of electrical signals to be applied to said body part; b) generating a plurality of variants by assembling the protocols stored in said central control device, or for generating combination of the variants by assembling the plurality of variants; and c) stimulating the body part by assigning each channel of said electrode with the protocols or variants, or combination of the variants of same or opposite frequency elements each other, wherein said electrode assigned with the protocols or the variants includes a single- or multi-channel with the same or opposite direction of electric currents on each channel.

In accordance with an embodiment of the present invention, there is provided an electrical stimulation method for use in an electrical clinical apparatus including a central control device for controlling electrical stimulation signals to be delivered to a body part via an electrode, wherein said electrode is in contact with a body part or is inserted into a body cavity for detecting EMG signals thereof or for applying the electrical stimulation signal thereto, and the electrical stimulation method comprising the steps of: a) receiving a protocol library from a communication equipment linked externally with said electrical clinical apparatus and storing the protocol library in said central control device or a memory thereof, wherein the protocol library includes protocols which is formed by a variation of electric signals applied to a body part in terms of pulse width, duty ratio, intensity/voltage of supplied electric current, burst duration, inter-burst interval as well as the frequencies; b) generating a plurality of variants by assembling the protocols stored in said central control device, or for generating combination of the variants by assembling the plurality of variants; and c) stimulating the body part by assigning each channel of said electrode with the protocols or variants, or combination of the variants of same or opposite frequency elements each other, wherein said electrode assigned with the protocols or the variants includes a single- or multi-channel with the same or opposite direction of electric currents on each channel.

In accordance with another embodiment of the present invention, there is provided an electrical stimulation method for use in an electrical clinical apparatus including an electrode and a central control device for controlling electrical stimulation signals, wherein said electrode is in contact with a body part or is inserted into a body cavity for detecting EMG signals thereof or for applying the electrical stimulation signals thereto, the electrical stimulation method comprising the steps of: a) creating a protocol library and storing the protocol library in said central control device, wherein the protocol library includes protocols formed by variation of target waveform signals presented to the body of a patient as a tool for assessing the EMG signals detected by said electrode; b) generating a plurality of variants by assembling the protocols stored in said central control device, or for generating combination of the variants by assembling the plurality of variants; and c) composing a target waveform with a plurality of EMG protocols or EMG variants containing different waveform characteristics each other out of the protocol library stored in said central control device, and for comparing the training goal waveform with a raw EMG waveform detected as a result of the actual exercise of the patients body part with the target waveform.

In accordance with further another embodiment of the present invention, there is provided an electrical stimulation method for use in an electrical clinical apparatus including an electrode and a central control device for controlling an electrode, wherein said electrode is in contact with a patient's body part or is inserted into a body cavity for stimulation by applying electric signals to the body part, the method comprising the steps of: a) forming a target waveform from a protocol library including EMG protocols, which are formed by modifying EMG signals detected from the body part by said electrode; and b) forming a raw waveform formed by the EMG signal detected from the patient's actual exercise so that the patient directly compares the target waveform with the raw waveform on a display device.

BRIEF DESCRIPTION OF THE DRAWINGS

Other objects and aspects of the invention will become apparent from the following description of the embodiments with reference to the accompanying drawings, in which.

DETAILED DESCRIPTION OF THE PREFERRED EMBODIMENTS

Figure 1:
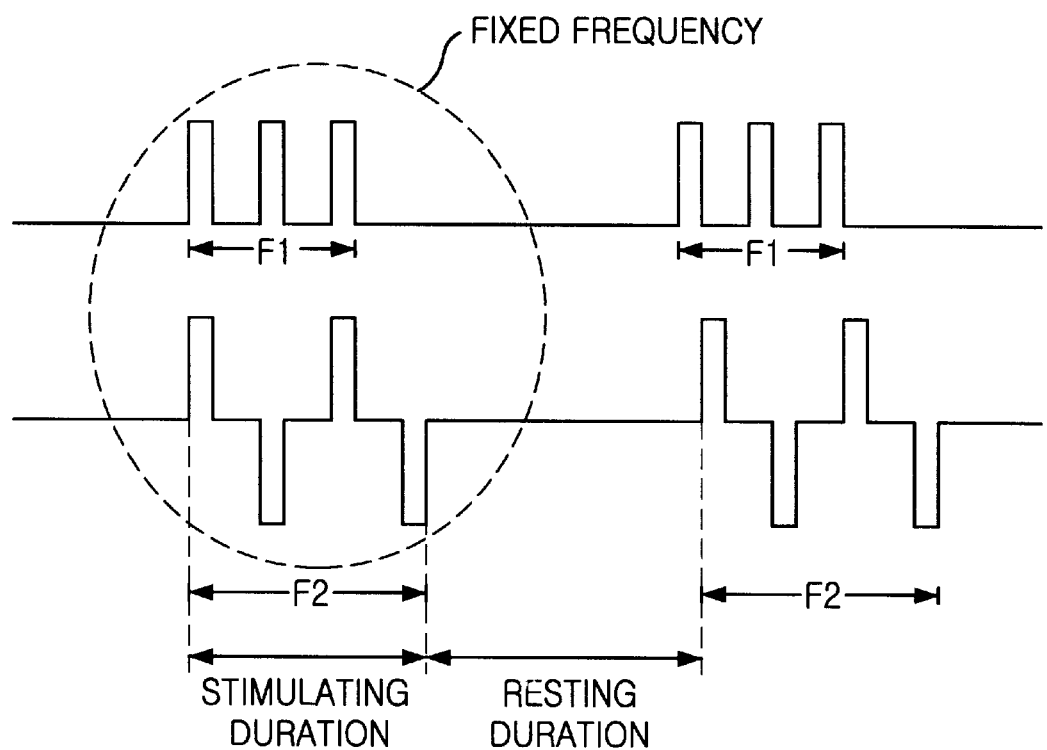
FIG. 1 shows a frequency movements in an electrical stimulation method using a conventional frequency fixed assignment method.
Figure 2A:
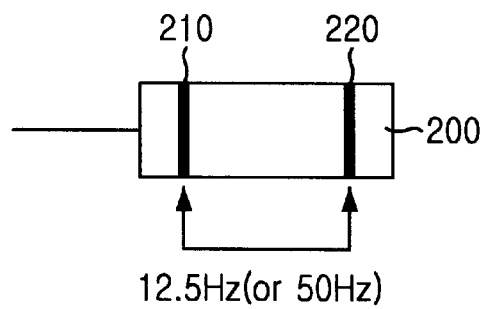
FIGS. 2A and 2B illustrate an electrode of an electrical clinical apparatus using a conventional frequency fixed assignment method.
Figure 2B:
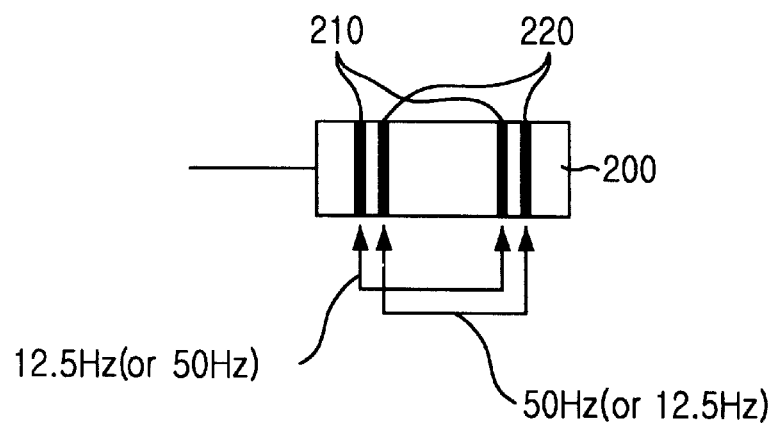

An electrical clinical apparatus, according to the present invention, relates to an apparatus for medical treatment by detecting raw electromyogram (EMG) signals in real time or by applying opposite mechanism of electrical stimulation signal to a body, particularly in such as a urinary incontinence treatment apparatus for treating urinary incontinence or a fecal incontinence treatment apparatus for treating fecal incontinence/constipation. In addition, the present invention includes electrodes which is in contact with a patient's body part to which treatment is applied for detecting the EMG signals or for applying electrical stimulation signal onto the muscular cell thereof. Such electrodes can be a tubular (or rod-shape) for insertion into a body cavity to which the treatment is applied or adhesive pad-type for adhering to a patient's body part to which the treatment is applied.

each other in terms of frequency, pulse width, duty ratio, intensity/voltage of supplied electric current, burst duration and inter-burst interval. The variable frequency, pulse width, duty ratio, intensity/voltage of the supplied electric current of electric signal may be pertinently settable according to the treatment purposes. For example, it may be settable at a frequency bandwidth of 1 to 1000 Hz, at a pulse width of 1000 to 10 μsec, at a biphasic rectangular or mono-phase rectangular pulse waveform, with Ramp-Up time+ Plateau time+ Ramp-Down time in the ratio of 1~5:1:1~5 for pulse burst duration and with burst duration and inter-burst interval in the ratio of 1:1~5 for inter-burst interval. Table 1 shows an example of the protocol library.

TABLE 1

| LIBRARY | INTENSITY | FREQUENCY | DUTY | PULSE WIDTH | BURST DURATION | INTER-BURST INTERVAL |
|---|---|---|---|---|---|---|
| PROTOCOL 1 | STRONG | LOW | BIG | WIDE | SHORT | LONG |
| PROTOCOL 2 | STRONG | LOW | BIG | WIDE | LONG | SHORT |
| PROTOCOL 3 | STRONG | LOW | BIG | WIDE | LONG | LONG |
| PROTOCOL 4 | STRONG | LOW | BIG | NARROW | SHORT | SHORT |
| PROTOCOL 5 | STRONG | LOW | BIG | NARROW | SHORT | LONG |
| PROTOCOL 6 | STRONG | LOW | BIG | NARROW | LONG | SHORT |
| PROTOCOL 7 | STRONG | LOW | BIG | NARROW | LONG | LONG |
| PROTOCOL 8 | WEAK | HIGH | SMALL | NARROW | SHORT | SHORT |
| PROTOCOL 9 | WEAK | HIGH | SMALL | NARROW | SHORT | LONG |
| PROTOCOL 10 | WEAK | HIGH | SMALL | NARROW | LONG | SHORT |
| PROTOCOL 11 | WEAK | HIGH | SMALL | NARROW | LONG | LONG |
| PROTOCOL 12 | WEAK | HIGH | SMALL | WIDE | SHORT | SHORT |
| PROTOCOL 13 | WEAK | HIGH | SMALL | WIDE | SHORT | LONG |
| PROTOCOL 14 | WEAK | HIGH | SMALL | WIDE | LONG | SHORT |
| PROTOCOL 15 | WEAK | HIGH | SMALL | WIDE | LONG | LONG |

Note: Such indications as high/low, wide/narrow, long/short are not accurately fixed values as they show smaller or larger value compared with a median value.

Hereafter, for the convenience of explanation, a urinary incontinence treatment apparatus will be described as an example.

As EMG biofeedback is the opposite mechanism of the electrical stimulation, only an example of electrical stimulation is to be described. However, those skilled in the art will appreciate that the present invention is not limited to the urinary incontinence treatment apparatus, but applied to other medical treatment apparatuses.

Figure 3:
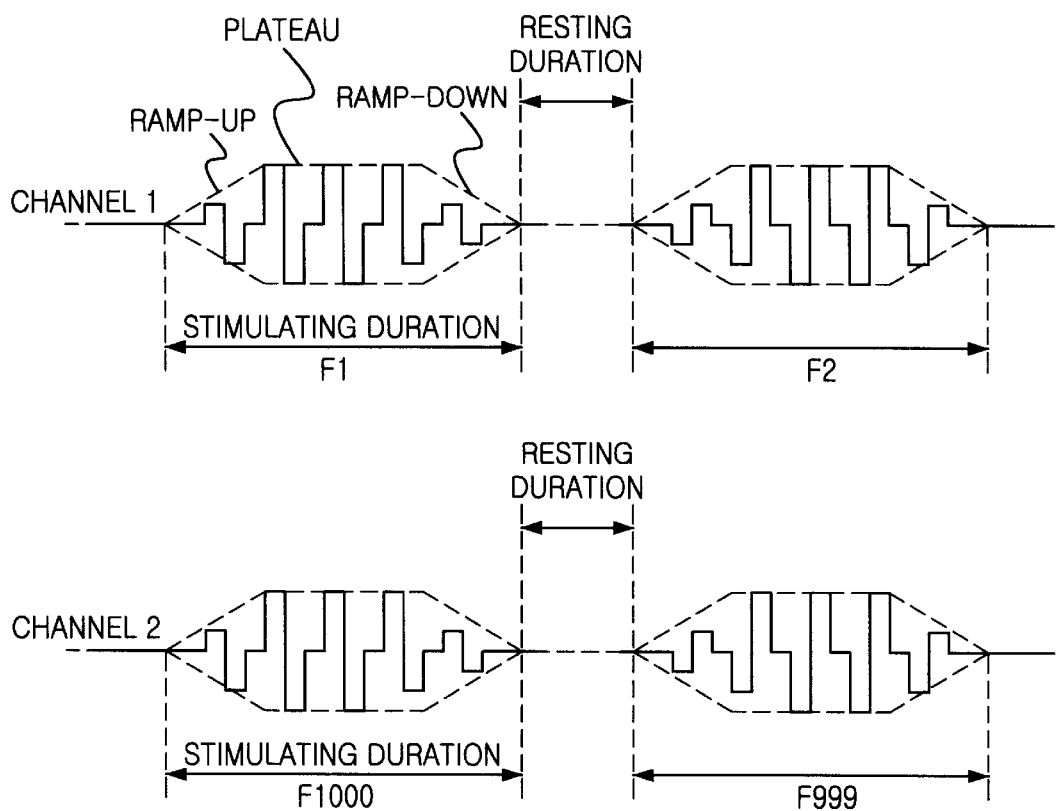
FIG. 3 shows a frequency movements in an electrical stimulation method using a frequency variant assignment method of the present invention.

FIG. 3 shows frequency movements of an electrical clinical apparatus using a frequency variant assignment method of the present invention. As shown in FIG. 3, the frequency bandwidth to be assigned on each channel of electrode mat vary between F1 (1 Hz) to F1000 (1000 Hz) in the present invention. Further, the duration of burst and rest can be adjusted freely, to which stimulation parameters can be arranged simultaneously or alternately on each channel at a certain point of time.

Electric characteristics are to be composed by changing or combining intensity, frequency, pulse width and duty ratio.

Figure 4:
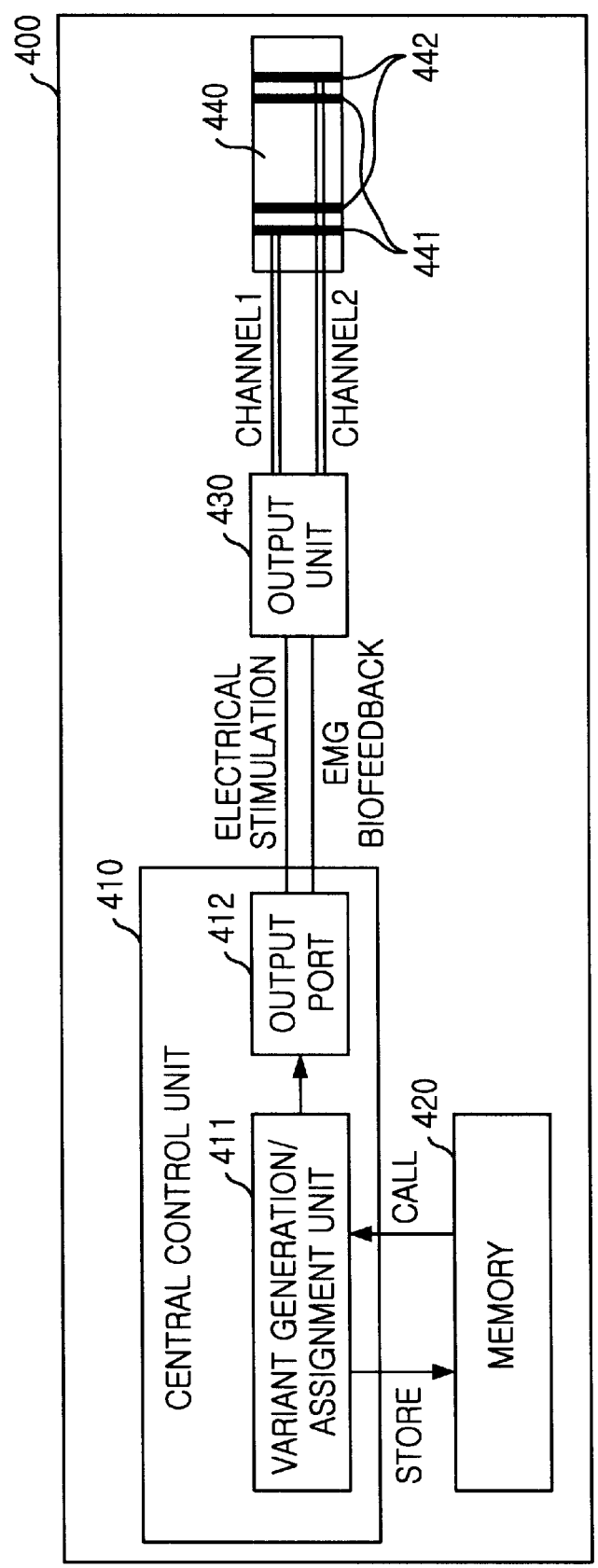
FIG. 4 is a block diagram of the electrical clinical apparatus using the frequency variant assignment method according to preferred embodiment of the present invention.

FIG. 4 shows a block diagram of the electrical clinical apparatus according to the preferred embodiment of the present invention configurable by using the frequency variant assignment method.

As illustrated in FIG. 4, the electrical clinical apparatus according to the present invention includes a central control device 410, a memory device 420, a power output circuit 430 and an electrode 440.

The central control device 410) produces a protocol library of which the protocols electric signals are different Such various protocols thus formed are to be assembled into variants in the variant generation/assignment section 411 of the central control device 410, or the variants are to be assembled into combinations of the variants. Each channel of the electrode 440 is to be assigned with the generated protocols, variants and combinations of variants.

For convenience of explanation, the preferred embodiment according to the present invention suppose that the electrode 440 is to have two channels thereon. However, those skilled in the art will appreciate that channels of electrode can be pertinently configured.

Figure 5:
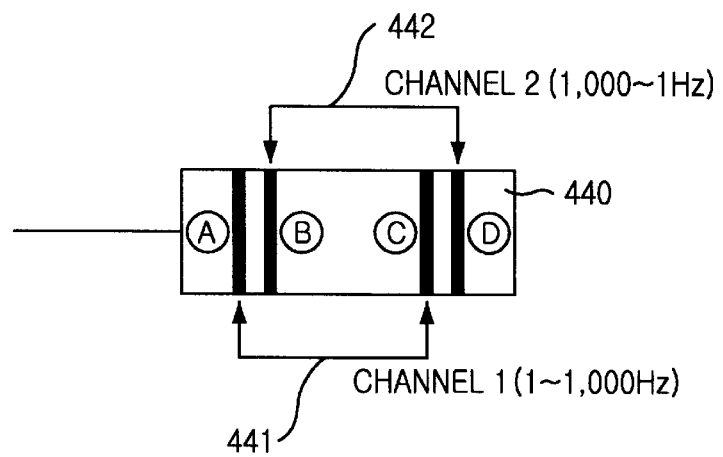
FIG. 5 illustrates an example of an electrode of the electrical clinical apparatus according to preferred embodiment of the present invention.

As illustrated in FIG. 5, the electrode 440 includes a first channel 441 and a second channel 442, and such channels can be configured with one or combined electric currents in the same direction or opposite direction. For example, the first channel 441 may be configured with A and D, A and C, or A and B while the second channel 442 can be configured with D and B, D and A, or D and C.

Hereafter, a method of assigning the first channel 441 and the second channel 442 of the electrode 440 with the protocols and variants will be described below.

If 120 or more protocols are to be generated, they will be serially applied during typically 30 minutes of an electrical stimulation session. For example, the first channel 441 is to be assigned with protocol 1, the second channel 442 is to be assigned with protocol 15 to protocol 2, and thus the first and second channels 441 and 442 are serially applied with the protocols different from each other. In addition to the method of assigning the two channels with the protocols different from each other, the same protocols may be assigned on both channels simultaneously. Table 2 shows an example of the assignment method of the protocols.

TABLE 2

| CHANNEL 1 | PROTOCOL 1 | VARIANT 1 | PROTOCOL 15 | CHANNEL 2 |
| --- | --- | --- | --- | --- |
| | PROTOCOL 2 | VARIANT 2 | PROTOCOL 14 | |
| | PROTOCOL 3 | VARIANT 3 | PROTOCOL 13 | |
| | PROTOCOL 4 | VARIANT 4 | PROTOCOL 12 | |
| | PROTOCOL 5 | VARIANT 5 | PROTOCOL 11 | |
| | PROTOCOL 6 | VARIANT 6 | PROTOCOL 10 | |
| | PROTOCOL 7 | VARIANT 7 | PROTOCOL 9 | |
| | PROTOCOL 8 | VARIANT 8 | PROTOCOL 8 | |
| | PROTOCOL 9 | VARIANT 9 | PROTOCOL 7 | |
| | PROTOCOL 10 | VARIANT 10 | PROTOCOL 6 | |
| | PROTOCOL 11 | VARIANT 11 | PROTOCOL 5 | |
| | PROTOCOL 12 | VARIANT 12 | PROTOCOL 4 | |
| | PROTOCOL 13 | VARIANT 13 | PROTOCOL 3 | |
| | PROTOCOL 14 | VARIANT 14 | PROTOCOL 2 | |
| | PROTOCOL 15 | VARIANT 15 | PROTOCOL 1 | |

Here, what is assembled by the protocols, which are different from each other, is called "variant." The variants also may be assembled into combinations of the variants, and the variants may be alternately assigned to each channel. The method of assigning channels with variants will be described as follows.

For example, the first channel is assigned with the variants of high frequency while the second channel is assigned with the variants of low frequency. Otherwise, the first channel is assigned with the variants of wide pulse width, while the second channel is assigned with the variants of narrow pulse width. That is, by assigning each channel of the electrode with signals of opposite frequency elements, energy applied to each channel of the electrode may be made different. In this case, the same results may be obtained by applying electrical stimulation onto the first and second channels 441 and 442 after changing intensity, duty ratio etc. The electrical stimulation is applied after serially assigning the first and second channels 441 and 442 with the variants different from each other until one session of treatment has been finished. Each channel may be assigned with one of the variants or combination of variants. Accordingly, all the variants to be applied may be configured in a form of variant 1+variant 2+ . . . +variant n, and table 3 shows such an example.

TABLE 3

| CONFIGURATION | CHANNEL 1 | CHANNEL 2 |
| --- | --- | --- |
| STIMULATION NO. 1 | VARIANT | — |
| STIMULATION NO. 2 | — | VARIANT |
| STIMULATION NO. 3. | VARIANT | VARIANT |

Functions of the variants may be applied to each channel of the electrode alternately or simultaneously. In case where stimulation serially applied to the body during one treatment session of about 15~30 minutes in total, such characteristics of variants internally carry out electrophysiological functions of reinnervating pelvic floor muscle nerve damaged due to childbirth and so on without causing any apparent discomfort. Such a phenomenon may be compared to the function of massage by the extremely deft and swift hands with electrophysiological effects peculiar to such electrical stimulation.

Here, the protocols having the variants are assigned not with a specific frequency but with wide range of frequency bandwidth of 1 to 1000 Hz impartially distributed, especially with emphasis on low frequency bandwidth of 1 to 200 Hz fit for human body. The reason is that effective frequencies are not fixed in a specific frequency even though most of them are distributed in relatively low bandwidth. That is, within 1~1000 Hz bandwidth, especially within low frequency bandwidth of 1~200 Hz, the frequencies induce contraction and relaxation of pelvic floor muscle as well as reinnervation of the nerve thereof, not being limited to a specific frequency. Accordingly, the stimulation of pelvic floor muscle with such frequencies may cover almost all the frequencies of patients so that consistent and stable treatment results may be obtained.

Figure 6:
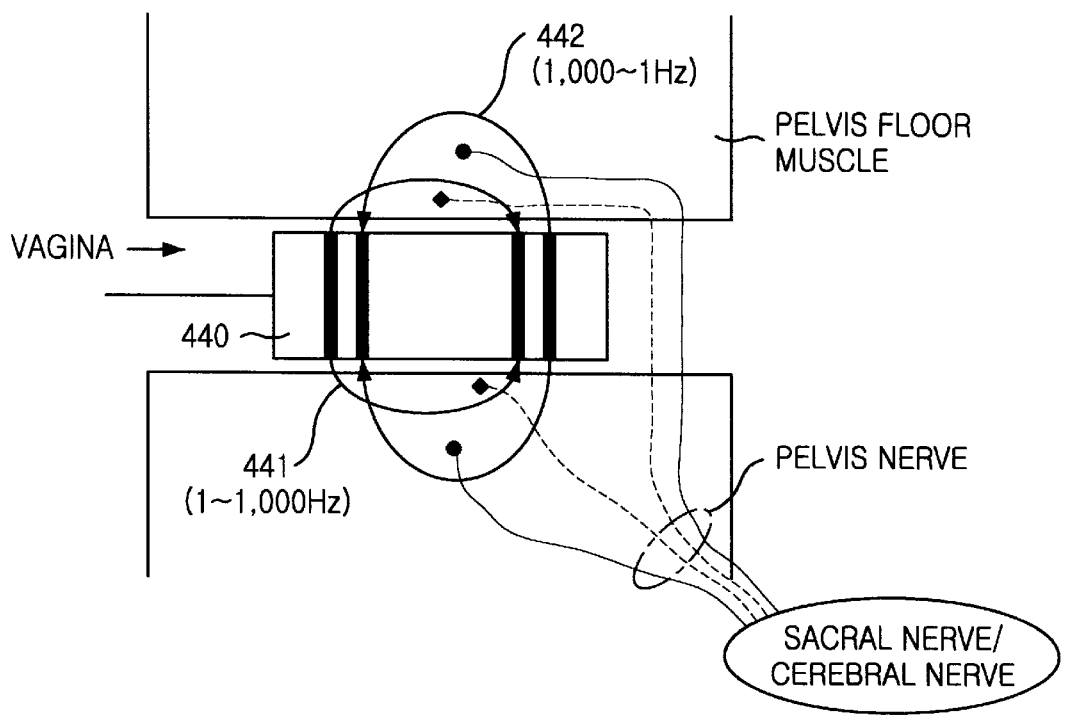
FIG. 6 illustrates an electrode and current directions thereon in the electrical clinical apparatus of the present invention applied to neuromuscular treatments.

Once protocols or variants to be assigned on each channel of the electrode are determined according to above-mentioned method, they are stored in the memory device 420 linked to the central control device 410. According to a fixed program, by a calling of the central control device 410, protocols and variants are transmitted again to the variant generation/assignment section 411 to be assigned on an output port 412 linked therewith, and then are to be transmitted to be assigned on each channel of electrode 440 through the output circuit 430 linked to the central control device 410. Thus, the first and second channels 441 and 442 of the electrode 440 finally receive the amplified signals by a hardware in the output circuit 430. As illustrated in FIG. 6, the electrode, Also, FIG. 6 illustrates how the electrode applies the stimulation onto the nerve and muscle of vagina by contacting thereto as an embodiment of the electrical stimulation method of the present invention.

Those skilled in the art will know that the present invention may be modified or amended in the context of a technical concept of the present invention. For example, the protocol library may be downloaded into the electrical clinical apparatus of the present invention, not in the method controlled by the incorporated central control device, namely through an externally connected communication equipment downloading into the central control device. Besides, the electrical clinical apparatus of the present invention may additionally includes a display device which displays a progress of electrical stimulation using graphic, character or small lamp and so on.

Figure 7:
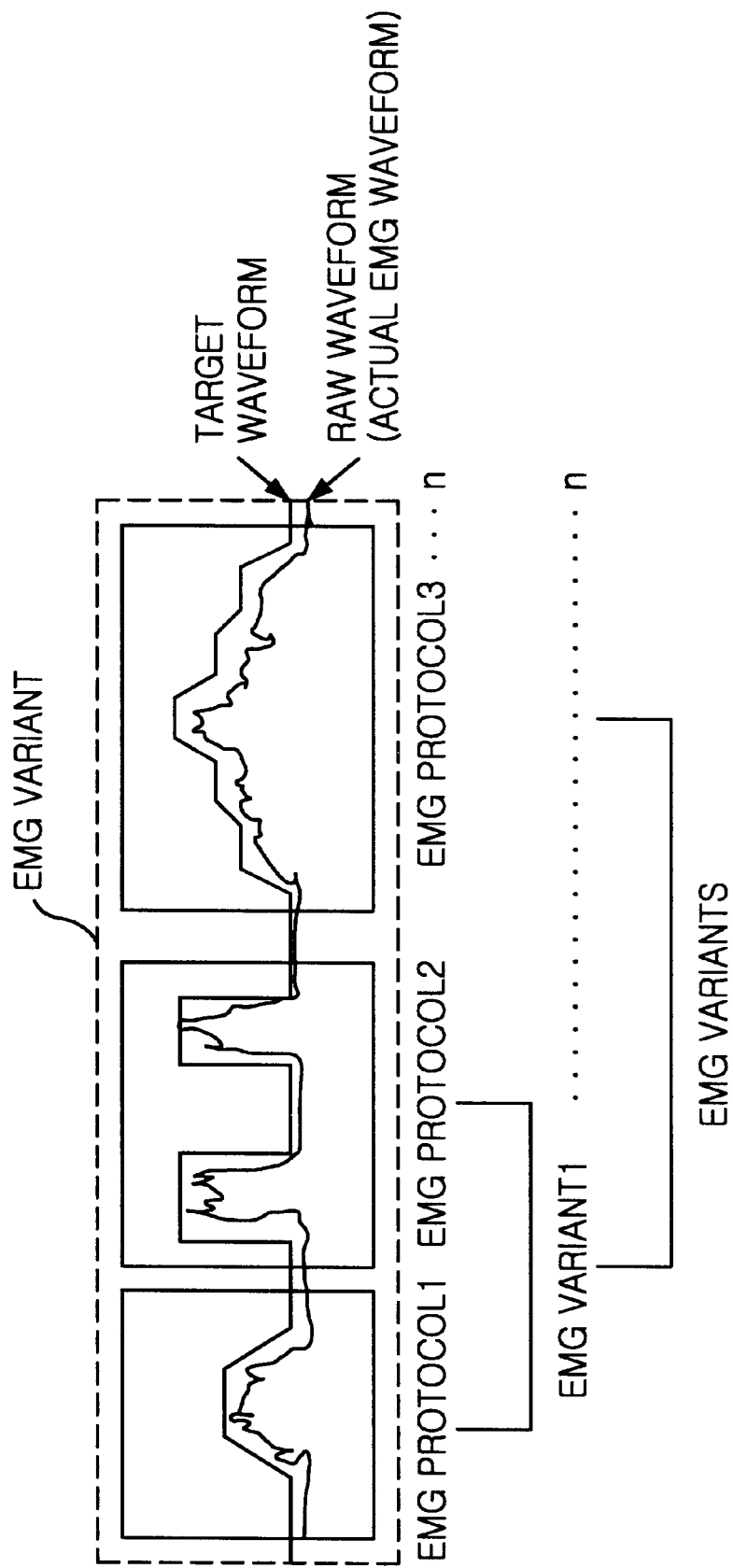
FIG. 7 illustrates a target waveform and an exercise waveform detected by the electrical clinical apparatus of the present invention.

As illustrated in FIG. 7, the electrical clinical apparatus of the present invention may raise the treatment effects of electrical clinical apparatus by inducing patients to match exercise waveforms to the target waveforms by concurrently displaying the two waveforms on the display device comprised in the electrical clinical apparatus, wherein the exercise waveform (or raw waveform) is to be the EMG signals detected as a result of the patient's actual exercise while the target waveform is to be selected from the protocol library including the EMG protocols (EMG protocol 1, EMG protocol 2, ..., EMG protocol n) formed by the variation of target waveforms to be presented to patients as a tool for assessing the EMG signals detected by the electrode. It is advisable to compose the target waveform by selecting those different waveform characteristics out of the EMG protocols or variants formed by assembling the EMG protocols, or out of combinations of the variants.

In the treatment of pelvic floor muscle damaged from childbirth and so on, as the present invention reinnervates the pelvic floor muscle nerve without causing any pain or discomforts that is frequently cited as the side effects of a conventional electrical stimulation method while resolving the tediousness of the EMG biofeedback and making the exercise interesting and consistently motivating, and as the variant protocols being used in the electrical stimulation contains all the treatment parameters for almost all the patients, the effects of consistent and stable treatment results may be gained. Besides, in the EMG biofeedback, the present invention may get the effects of raising the treatment effects by composing diversified target waveforms for the patient to exercise without feeling tedious.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. An electrical clinical apparatus including an electrode, which is in contact with a body part or is inserted into a body cavity, for detecting electromyogram (EMG) signals thereof or for applying electrical stimulation signals thereto, the electrical clinical apparatus comprising:

a central control device for forming a plurality of protocols by varying frequencies of the electrical signals to be applied to a body part, and for generating a plurality of variants by assembling the protocols, and for respectively selecting protocols or variants to be assigned to each channel of said electrode out of the protocols and variants;

a memory device for storing the protocols or variants produced by said central control device, or for re-inputting the stored protocols or variants back to said central control device according to a predetermined program; and an output device for outputting the selected protocol or variant to each channel of said electrode, wherein said electrode assigned with the protocols or variants of choice includes a single- or multi-channel in the same or opposite direction of current and wherein the selected protocols or variants are characterized by the same or opposite electric characteristics each other.

2. The electrical clinical apparatus recited in claim 1, wherein said electrode comprises vaginal insertion type or epidermis attachment patch type probes, each channel of which conduct the same or opposite direction of currents each other, and wherein the selected protocols or variants assigned onto said electrode have the same or opposite electrical characteristics.

3. The electrical clinical apparatus recited in claim 1, wherein said central control device includes an output port for outputting the protocols or variants to said output device.

4. The electrical clinical apparatus recited in claim 1, wherein said central control device assigns each channel of said electrode with electrical signals containing opposite frequency elements each other by serially assigning each channel with the protocols or variants, or combinations of the variants, or by alternately assigning the same protocols or variants, or the same combinations of the variants on each channel of said electrode.

5. The electrical clinical apparatus recited in claim 4, wherein the protocols are at a frequency of 1 to 1000 Hz.

6. The electrical clinical apparatus recited in claim 5, wherein the protocols include pulse width, duty ratio, intensity/voltage of supplied electric current by ramp-up, plateau and ramp-down, burst duration and inter-burst interval as stimulation parameters as well as variation of frequencies of electrical signals different from each other.

7. An electrical clinical apparatus including an electrode, which is in contact with a body part or is inserted into a body cavity, for detecting electromyogram (EMG) signals thereof or for applying electrical stimulation signals thereto, the electrical clinical apparatus comprising:

a central control device for assigning each channel of said electrode with protocols or variants which are inputted through a communication equipment connected externally into said electrical clinical apparatus, wherein the protocols are formed by a conversion of electric signals to be delivered to the body part in terms of pulse width, duty ratio, intensity/voltage of supplied electric current, burst duration, and inter-burst interval as well as frequencies and the variants are formed by assembling the protocols; and an output device for outputting the assigned protocols or variants by said central control device into each channel of said electrode, wherein said electrode assigned with the protocols or variants includes a single- or multi-channel with the same or opposite direction of electric currents on each channel and wherein the assigned protocols or variants have the same or opposite electrical characteristics each other.

8. An electrical stimulation method through an electrical clinical apparatus including an electrode and a central control device for controlling said electrode, wherein said electrode is in contact with a body part or is inserted into a body cavity for stimulating thereto by applying electrical signals, the electrical stimulation method comprising the steps of:

a) creating a protocol library and storing the protocol library in said central control device or a memory of the electrical clinical apparatus, wherein the protocol library includes protocols formed by a frequency variation of electrical signals to be applied to the body part;

b) generating a plurality of variants by assembling the protocols stored in said central control device, or for generating combination of the variants by assembling the plurality of variants; and c) stimulating the body part by assigning each channel of said electrode with the protocols or variants, or combination of the variants of same or opposite frequency elements each other, wherein said electrode assigned with the protocols or the variants includes a single- or multi-channel with the same or opposite direction of electric currents on each channel.

9. The electrical stimulation method recited in claim 8, further comprising d) displaying a progress of electrical stimulation involved with the variants by means of graphics, characters or tiny lamps on a display device incorporated in or linked externally with said electrical clinical apparatus.

10. The electrical stimulation method recited in claim 8, wherein the step b) includes a step of assigning each channels of said with electrode electrical signals containing the same or opposite frequency elements by serially assigning each channel with the protocols or variants, or combination of the variants, or by assigning the same protocols or variants, or combination of the variants alternately, reciprocally, synchronously, asynchronously on each different channel.

11. The electrical stimulation method recited in claim 10, wherein the protocols are at a frequency of 1 to 1000 Hz.

12. The electrical stimulation method recited in claim 11, wherein the protocols include a variation of electric signals different from each other in terms of pulse width, duty ratio, intensity/voltage of supplied electric current, burst duration and inter-burst interval as well as the variation of frequencies.

13. An electrical stimulation method, for use in an electrical clinical apparatus including a central control device for controlling electrical stimulation signals to be delivered to a body part via an electrode, wherein said electrode is in contact with a body part or is inserted into a body cavity for detecting electromyogram (EMG) signals thereof or for applying the electrical stimulation signal thereto, and the electrical stimulation method comprising the steps of:

a) receiving a protocol library from a communication equipment linked externally with said electrical clinical apparatus and storing the protocol library in said central control device or a memory thereof, wherein the protocol library includes protocols which is formed by a variation of electric signals applied to a body part in terms of pulse width, duty ratio, intensity/voltage of supplied electric current, burst duration, inter-burst interval as well as the frequencies;

b) generating a plurality of variants by assembling the protocols stored in said central control device, or for generating combination of the variants by assembling the plurality of variants; and c) stimulating the body part by assigning each channel of said electrode with the protocols or variants, or combination of the variants of same or opposite frequency elements each other, wherein said electrode assigned with the protocols or the variants includes a single- or multi-channel with the same or opposite direction of electric currents on each channel.

14. An electrical stimulation method, for use in an electrical clinical apparatus including an electrode and a central control device for controlling electrical stimulation signals, wherein said electrode is in contact with a body part or is inserted into a body cavity for detecting electromyogram (EMG) signals thereof or for applying the electrical stimulation signals thereto, the electrical stimulation method comprising the steps of:

a) creating a protocol library and storing the protocol library in said central control device, wherein the protocol library includes protocols formed by variation of target waveform signals presented to the body of a patient as a tool for assessing the electromyogram (EMG) signals detected by said electrode;

b) generating a plurality of variants by assembling the protocols stored in said central control device, or for generating combination of the variants by assembling the plurality of variants; and c) composing a target waveform with a plurality of electromyogram (EMG) protocols or electromyogram (EMG) variants containing different waveform characteristics each other out of the protocol library stored in said central control device, and for comparing a training goal waveform with a raw electromyogram (EMG) waveform detected as a result of the actual exercise of the patients body part with the target waveform.

15. The electrical stimulation method recited in claim 14, further comprising d) simultaneously displaying said target waveform together with the raw electromyogram (EMG) waveform on a display device incorporated in or externally linked to said electrical clinical apparatus.

16. An electrical stimulation method, for use in an electrical clinical apparatus including an electrode and a central control device for controlling an electrode, wherein said electrode is in contact with a patient's body part or is inserted into a body cavity for stimulation by applying electric signals to the body part, the method comprising the steps of:

a) forming a target waveform from a protocol library including electromyogram (EMG) protocols, which are formed by modifying electromyogram (EMG) signals detected from the body part by said electrode; and b) forming a raw waveform formed by the electromyogram (EMG) signal detected from the patient's actual exercise so that the patient directly compares the target waveform with the raw waveform on a display device.

* * * * *